(12) United States Patent
Ruiz Del Agua et al.

(10) Patent No.: US 10,215,762 B2
(45) Date of Patent: Feb. 26, 2019

(54) METHOD TO OPTIMIZE THE TREATMENT OF PATIENTS WITH BIOLOGICAL DRUGS

(71) Applicant: PROGENIKA BIOPHARMA, S.A., Derio (Bizkaia) (ES)

(72) Inventors: Ainhoa Ruiz Del Agua, Derio (ES); Antonio Martinez Martinez, Derio (ES); Daniel Nagore Casas, Derio (ES); Laureano Simon Buela, Derio (ES)

(73) Assignee: Progenika Biopharma, S.A., Derio (Bizkaia) (ES)

( * ) Notice: Subject to any disclaimer, the term of this patent is extended or adjusted under 35 U.S.C. 154(b) by 154 days.

(21) Appl. No.: 15/281,829

(22) Filed: Sep. 30, 2016

(65) Prior Publication Data

US 2017/0102394 A1  Apr. 13, 2017

Related U.S. Application Data

(63) Continuation of application No. 13/997,069, filed as application No. PCT/EP2011/073836 on Dec. 22, 2011.

(30) Foreign Application Priority Data

Dec. 22, 2010  (EP) .................................. 10382346

(51) Int. Cl.
| | |
|---|---|
| *A61K 39/00* | (2006.01) |
| *C07K 16/24* | (2006.01) |
| *G01N 33/68* | (2006.01) |
| *G01N 33/564* | (2006.01) |
| *G01N 33/94* | (2006.01) |
| *A61K 39/395* | (2006.01) |
| *A61K 49/00* | (2006.01) |
| *G06F 19/00* | (2018.01) |

(52) U.S. Cl.
CPC ..... *G01N 33/6893* (2013.01); *A61K 39/3955* (2013.01); *A61K 49/00* (2013.01); *C07K 16/241* (2013.01); *G01N 33/564* (2013.01); *G01N 33/6854* (2013.01); *G01N 33/9493* (2013.01); *G06F 19/00* (2013.01); *G06F 19/325* (2013.01); *G06F 19/3468* (2013.01); *C07K 2317/21* (2013.01); *C07K 2317/24* (2013.01); *G01N 2333/525* (2013.01); *G01N 2800/102* (2013.01); *G01N 2800/24* (2013.01); *G01N 2800/52* (2013.01); *Y02A 90/26* (2018.01)

(58) Field of Classification Search
None
See application file for complete search history.

(56) References Cited

PUBLICATIONS

International Search Report dated Mar. 28, 2012 in corresponding Application No. PCT/EP2011/073836, filed Dec. 22, 2011, 8 pages.
Bartelds Geertje M. et al., "Clinical response to adalimumab: relationship to anti-adalimumab antibodies and serum adalimumab concentrations in rheumatoid arthritis", Annals of the Rheumatic Diseases, British Medical Association. London, GB, Jul. 1, 2007, vol. 66, No. 7, pp. 921-926.
Bartelds Geertje M. et al., "Development of antidrug antibodies against adalimumab and association with disease activity and treatment failure during long-term follow-up", JAMA, Apr. 13, 2011, pp. 1460-1468.
Nadia Emi Aikawa et al., "Immunogenicity of anti-TNF-[alpha] agents in autoimmune diseases", Clinical Reviews in Allergy and Immunology, Apr. 1, 2010, vol. 38, No. 2-3, pp. 82-89.
Pascual-Salcedo Dora et al., "Influence of Immunogenicity on the efficacy of long-term treatment with infliximab in rheumatoid arthritis", Rheumatology (Oxford, England), Aug. 2011, vol. 50, No. 8, web publication, 8 pages.
Radstake et al., "Formation of antibodies against infliximab and adalimumab correlates with functional drug levels and clinical responses in rheumatoid arthritis", Annals of the Rheumatic Diseases, vol. 68, 2009, pp. 1739-1745.
Rosas-Gomez de Salazar Jose et al., "Evaluation of anti-tumor necrosis factor levels and anti-tumor necrosis factor antibodies in rheumatic diseases treated with infliximab and adalimumab; preliminary results from a local registry", Arthritis and Rheumatism, Oct. 2011, vol. 63, No. 10, Suppl. S. p. S863, web publication.
Ruiz Del Agua et al, "Monitoring of anti-TNF biological treatments", Journal of Translational Medicine, Nov. 25, 2010, vol. 8, No. S1, p. 32, web publication.
Shunsuke Mori, "A relationship between pharmacokinetics (PK) and the efficacy of infliximab for patients with rheumatoid arthritis: characterization of infliximab-resistant cases and PK-based modified therapy", Modern Rheumatology; Official Journal of the Japan College of Rheumatology, Springer-Verlag, TO, Apr. 20, 2007, vol. 17, No. 2, pp. 83-91 (Abstract Only), 2 pages.
Wolbink G.J. et al., "Relationship between serum through infliximab levels, pretreatment C reactive protein levels, and clinical response to infliximab treatment in patients with rheumatoid arthritis", Annals of the Rheumatic Diseases, British Medical Association, London, GB, May 1, 2005, vol. 64, No. 5, pp. 704-707.
Van der Bijl et al., "An open-label pilot study of the effectiveness of adalimumab in patients with rheumatoid arthritis and previous infliximab treatment: relationship to reasons for failure and anti-infliximab antibody status", Clinical Rheumatology, 2007, vol. 27, pp. 1021-1028.
Non Final Office Action for U.S. Appl. No. 13/997,069, dated Mar. 18, 2015, 15 pages.
Final Office Action for U.S. Appl. No. 13/997,069, dated Aug. 10, 2015, 9 pages.

*Primary Examiner* — Julie Wu
(74) *Attorney, Agent, or Firm* — Dinsmore & Shohl LLP

(57) ABSTRACT

The invention relates to the field of personalized therapy and, in particular, to a method for classifying a patient suffering from rheumatoid arthritis as a responder or as a non-responder patient to a treatment based on a biological drug.

11 Claims, 3 Drawing Sheets
Specification includes a Sequence Listing.

SEQUENCE LISTING

```
<160> NUMBER OF SEQ ID NOS: 2

<210> SEQ ID NO 1
<211> LENGTH: 233
<212> TYPE: PRT
<213> ORGANISM: Homo sapiens

<400> SEQUENCE: 1

Met Ser Thr Glu Ser Met Ile Arg Asp Val Glu Leu Ala Glu Glu Ala
1               5                   10                  15

Leu Pro Lys Lys Thr Gly Gly Pro Gln Gly Ser Arg Arg Cys Leu Phe
            20                  25                  30

Leu Ser Leu Phe Ser Phe Leu Ile Val Ala Gly Ala Thr Thr Leu Phe
        35                  40                  45

Cys Leu Leu His Phe Gly Val Ile Gly Pro Gln Arg Glu Glu Phe Pro
    50                  55                  60

Arg Asp Leu Ser Leu Ile Ser Pro Leu Ala Gln Ala Val Arg Ser Ser
65                  70                  75                  80

Ser Arg Thr Pro Ser Asp Lys Pro Val Ala His Val Val Ala Asn Pro
                85                  90                  95

Gln Ala Glu Gly Gln Leu Gln Trp Leu Asn Arg Arg Ala Asn Ala Leu
            100                 105                 110

Leu Ala Asn Gly Val Glu Leu Arg Asp Asn Gln Leu Val Val Pro Ser
        115                 120                 125

Glu Gly Leu Tyr Leu Ile Tyr Ser Gln Val Leu Phe Lys Gly Gln Gly
```

```
                    130                 135                 140
Cys Pro Ser Thr His Val Leu Leu Thr His Thr Ile Ser Arg Ile Ala
145                 150                 155                 160

Val Ser Tyr Gln Thr Lys Val Asn Leu Leu Ser Ala Ile Lys Ser Pro
                165                 170                 175

Cys Gln Arg Glu Thr Pro Glu Gly Ala Glu Ala Lys Pro Trp Tyr Glu
                180                 185                 190

Pro Ile Tyr Leu Gly Gly Val Phe Gln Leu Glu Lys Gly Asp Arg Leu
                195                 200                 205

Ser Ala Glu Ile Asn Arg Pro Asp Tyr Leu Asp Phe Ala Glu Ser Gly
                210                 215                 220

Gln Val Tyr Phe Gly Ile Ile Ala Leu
225                 230

<210> SEQ ID NO 2
<211> LENGTH: 164
<212> TYPE: PRT
<213> ORGANISM: Homo sapiens

<400> SEQUENCE: 2

Met His His His His His Val Arg Ser Ser Arg Thr Pro Ser
1               5                   10                  15

Asp Lys Pro Val Ala His Val Val Ala Asn Pro Gln Ala Glu Gly Gln
                20                  25                  30

Leu Gln Trp Leu Asn Arg Arg Ala Asn Ala Leu Leu Ala Asn Gly Val
                35                  40                  45

Glu Leu Arg Asp Asn Gln Leu Val Val Pro Ser Glu Gly Leu Tyr Leu
                50                  55                  60

Ile Tyr Ser Gln Val Leu Phe Lys Gly Gln Gly Cys Pro Ser Thr His
65                  70                  75                  80

Val Leu Leu Thr His Thr Ile Ser Arg Ile Ala Val Ser Tyr Gln Thr
                85                  90                  95

Lys Val Asn Leu Leu Ser Ala Ile Lys Ser Pro Cys Gln Arg Glu Thr
                100                 105                 110

Pro Glu Gly Ala Glu Ala Lys Pro Trp Tyr Glu Pro Ile Tyr Leu Gly
                115                 120                 125

Gly Val Phe Gln Leu Glu Lys Gly Asp Arg Leu Ser Ala Glu Ile Asn
                130                 135                 140

Arg Pro Asp Tyr Leu Asp Phe Ala Glu Ser Gly Gln Val Tyr Phe Gly
145                 150                 155                 160

Ile Leu Ala Leu
```

METHOD TO OPTIMIZE THE TREATMENT OF PATIENTS WITH BIOLOGICAL DRUGS

CROSS REFERENCE TO RELATED APPLICATIONS

This application is a continuation application of U.S. application Ser. No. 13/997,069, filed Jun. 21, 2013, which itself is the U.S. National Phase application of PCT International Application No. PCT/EP2011/073836, filed Dec. 22, 2011, and claims priority to European Patent Application No. EP 10382346.4, filed Dec. 22, 2010, the disclosures of which are incorporated by reference in their entirety for all purposes.

FIELD OF THE INVENTION

The present invention relates to the field of personalized therapy and, in particular, to a method for classifying a patient suffering from rheumatoid arthritis as a responder or as a non-responder patient to a treatment based on a biological drug selected from infliximab and adalimumab.

BACKGROUND OF THE INVENTION

The use of biological drugs has increased during the last years. For example, the TNF-alpha neutralizing antibodies are increasingly being used to treat diseases with a strong inflammatory background like rheumatoid arthritis (RA) and Inflammatory Bowel Disease (IBD).

Chronic inflammatory diseases represent a group of heterogeneous conditions characterized by an elevated production of cytokines, molecules which are essential for an organism's immune response, that play a critical role in the pathology of these diseases. Among the many cytokines Tumor Necrosis Factor alpha (TNF-alpha) is a key player due to its role in initiating the cascade of inflammatory processes and thus for triggering the development of disease symptoms in individuals suffering from an inflammatory disease.

The latest generation of biological drugs for the treatment of inflammatory diseases is based on antibody constructs that exert their effect by binding to TNF-alpha thus blocking initiation of the inflammatory cascade. While potentially very effective the use of these drugs requires the patient's response to the treatment to be closely monitored in order, if necessary, to guide the treatment regime.

In practice the response to treatment of patients with autoimmune and inflammatory diseases is monitored based on a number of clinical variables that reflect aspects of the disease process. Increasing the uniformity and consistency of methods used to measure patient response to treatment with anti-TNF-alpha biological drugs will help in optimizing dosing and contribute to a better use of expensive therapeutics by health care providers for the benefit of their patients.

Due to their structure and nature anti-TNF-alpha biological drugs are highly immunogenic. Unfortunately an immune response in the patient against biological drugs can dramatically reduce the efficacy of treatment.

Therefore, there is a need in the art for methods suitable for the determination of the patient response to a treatment based in a biological drug that are more specific than the conventional methods, and particularly for methods suitable for determining the response of a patient suffering from rheumatoid arthritis to a treatment based in an anti-TNF-alpha biological drug selected from infliximab and adalimumab.

DETAILED DESCRIPTION OF THE INVENTION

Definitions

Figure 1:
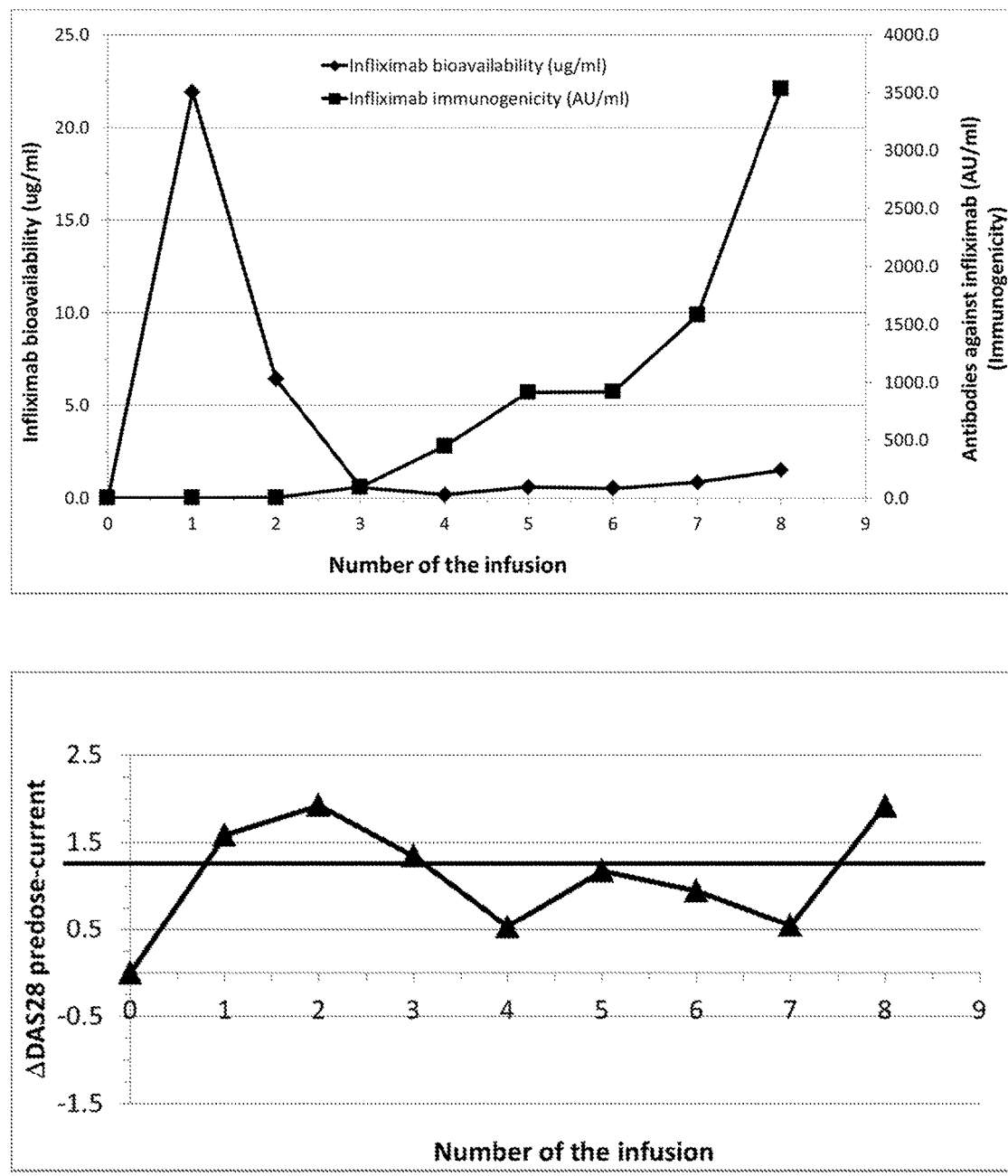
FIG. 1. Infliximab bioavailability and immunogenicity profiles over one year of treatment (top). The average values are shown for the group of patients showing no response to infliximab. ΔDAS28 is indicated for each infusion time (bottom). ΔDAS28 does not increase over the year of treatment (bottom). The horizontal line in the bottom panel indicates the ΔDAS28=1.2 threshold.

The term "antibody" (also known as immunoglobulins, abbreviated Ig), as used herein is intended to gamma-globulin proteins that are found in blood or other bodily fluids of vertebrates, and that can bind to a target in an specific way. They are typically made of basic structural units, each with two large heavy chains and two small light chains, to form, for example, monomers with one unit, dimers with two units or pentamers with five units. The antibodies that can be used in the present invention as biological drugs, directed to different targets, are commercial products or can be obtained by conventional methods known by the person skilled in the art. Also antibody fragments can be used. An antibody fragment is a fragment of an antibody such as, for example, Fab, F(ab')2, Fab', scFv, diabodies, etc. Various techniques have been developed for the production of antibody fragments. Traditionally, these fragments were derived via proteolytic digestion of intact antibodies but more recently these fragments can be produced directly by recombinant host cells. Papain digestion of antibodies produces two identical antigen-binding fragments, called "Fab'" fragments, each with a single antigen-binding site, and a residual "Fc" fragment. Pepsin treatment yields an F(ab')2 fragment that has two antigen-binding sites and is still capable of cross-linking antigen. "Fv" is the minimum antibody fragment which contains a complete antigen-recognition and antigen-binding site. Fab' fragments differ from Fab fragments by the addition of a few residues at the carboxy terminus of the heavy chain CH1 domain including one or more cysteines from the antibody hinge region. Other chemical couplings of antibody fragments are also known. A single chain Fv (scFv) fragment comprises the VH and VL domains of an antibody, wherein these domains are present in a single polypeptide chain, and may be monospecific or bispecific. The term "diabodies" refers to small antibody fragments with two antigen-binding sites, which fragments comprise a heavy-chain variable domain (VH) connected to a light chain variable domain (VL) in the same polypeptide chain (VH-VL).

By "anti-TNF-alpha (or "anti-TNF-α", or "anti-TNF-α" or simply "anti-TNF") therapy (or treatment)" is meant the administration to a patient of a biological drug or biological molecule (biopharmaceutical) capable of blocking, inhibiting, neutralizing, preventing receptor binding, or preventing TNFR activation by TNF-alpha. TNFR ("tumor necrosis factor receptor"), or death receptor, is a cytokine receptor that binds tumor necrosis factors (e.g., TNF-alpha) (Locksley R M, et al. 2001. Cell 104 (4): 487-501). Illustrative, non-limitative examples of such biological drugs include inhibitory antibodies against TNF-alpha as well as compounds, other than antibodies, capable of binding to TNF-alpha, e.g., proteins, peptides, small chemical molecules, etc.

The term "biological drug", as used herein, refers to any substance made or obtained from a living organism or its products that is used in the prevention, diagnosis or treatment of a pathology, e.g., a human pathology, like antibodies such as IgG-like antibodies, Fab fragments, etc.; thus, a biological drug or biopharmaceutical is a medical drug produced using biotechnology, for example, a protein (including antibodies), a nucleic acid (DNA, RNA or antisense oligonucleotides), used for therapeutic or in vivo diagnostic purposes, and, generally are produced by means other than direct extraction from a native (non-engineered) biological source.

The term "dose" or "therapeutically effective amount" is used herein to mean an amount sufficient to prevent, and preferably reduce by at least about 25 percent, more preferably by at least 50 percent, most preferably by at least 90 percent, a clinically significant change in a feature of pathology. As related to the present invention, the term may also mean an amount sufficient to ameliorate or reverse one or more symptoms associated with a disease.

By "rheumatoid arthritis" or "RA" is meant a chronic, systemic inflammatory disorder that may affect many tissues and organs, but principally attacks synovial joints. The process produces an inflammatory response of the synovium (synovitis) secondary to hyperplasia of synovial cells, excess synovial fluid, and the development of pannus in the synovium. The pathology of the disease process often leads to the destruction of articular cartilage and ankylosis of the joints. Rheumatoid arthritis can also produce diffuse inflammation in lungs, pericardium, pleura, and sclera, and also nodular lesions, most common in subcutaneous tissue under the skin. Although the cause of RA is unknown, autoimmunity plays a pivotal role in both its chronicity and progression, and RA is considered as a systemic autoimmune disease.

The term "patient", as used herein, refers to all animals classified as mammals and includes, but is not restricted to, domestic and farm animals, primates and humans, e.g., human beings, non-human primates, cows, horses, pigs, sheep, goats, dogs, cats, or rodents. Preferably, the patient is a male or female human of any age or race.

The term "sample", as used herein, relates to any sample which can be obtained from the patient, namely, a sample susceptible of containing antibodies. Thus, the present method can be applied to practically any type of biological sample from a patient, such as a biopsy sample, tissue, cell or fluid, e.g., blood, brain extracts, cerebral spinal fluid (CSF), milk, mucus, plasma, saliva, semen, serum, sputum, sweat, tears, and the like. In a particular embodiment, said sample is selected from blood, plasma or serum.

The term "TNF-alpha" (abbreviated herein as "TNF-α", "TNFa" or simply "TNF"), as used herein, is intended to refer to a human cytokine that exists as a 17 kD secreted form and a 26 kD membrane associated form, the biologically active form of which is composed of a trimer of noncovalently bound 17 kD molecules. The sequence of human TNF-alpha is shown in CAA26669.1 (SEQ ID NO: 1). The term "TNF-alpha" as used herein not only includes the human gene and protein but also their orthologues from other species such as dogs, mice, rats, etc., as well as functionally equivalent variants thereof.

Method of the Invention

The authors of the present invention have now found that a specific concentration of a circulating biological drug (e.g., infliximab, adalimumab, etc.) together with, optionally, a specific concentration of antibodies to said biological drug (anti-biological drug antibodies), particularly as determined in a blood sample from a patient, said patient suffering from rheumatoid arthritis and being treated with said biological drug, is associated with the patient's response to the treatment with said biological drug.

This information would allow physicians (medical doctors) to follow more closely their patients' response to treatment and to make informed decisions over treatment. These biological variables have been clinically validated to show utility in correlating both the levels of circulating biological drugs and the levels of antibodies against said biological drugs with the efficacy of treatment based on the patients Disease Activity Score (DAS28) used to follow up the disease in patients.

Thus, in an aspect, the present invention refers to a method, hereinafter referred to as the "method of the invention", for classifying a patient suffering from rheumatoid arthritis as a responder or as a non-responder patient to a treatment, said treatment comprising the administration to said patient of a biological drug selected from the group consisting of infliximab and adalimumab that is periodically administered by repetitive administrations, and wherein said patient has received at least one dose from said biological drug, said method comprising the steps of:
  a) determining the concentration of the circulating biological drug in a sample from said patient at a time t1 wherein said t1 corresponds to a time point within the period of time between two successive administrations of said biological drug; and
  b) comparing the concentration of the circulating biological drug at said t1 with a Reference Value 1 (RV1),
wherein
  RV1 is a therapeutic efficiency cut-off value of the concentration of the circulating biological drug; and
wherein if the concentration of the circulating biological drug is lower than RV1, then said patient is classified as a non-responder patient to said treatment, and
wherein if the concentration of the circulating biological drug is equal to, or higher than, RV1, then said patient is classified as a responder patient to said treatment, and
wherein if the biological drug is infliximab, then RV1 is 1.5 µg/ml; and
wherein if the biological drug is adalimumab, then RV1 is 0.8 µg/ml.

In the method of the invention, the pathology which is treatable with a biological drug is a pathology wherein TNF-alpha is involved, specifically rheumatoid arthritis. The patient is subjected to an anti-TNF-alpha treatment comprising the administration to said patient of a biological drug selected from the group consisting of infliximab and adalimumab that is periodically administered by repetitive administrations, said biological drug being capable of blocking, inhibiting, neutralizing, preventing receptor binding, or preventing TNFR activation by TNF-alpha.

Said biological drug is an antibody or a fragment thereof; particularly, an inhibitory anti-TNF-alpha antibody. An "inhibitory anti-TNF-alpha antibody" or "inhibitory antibody against TNF-alpha", as used herein, refers to an antibody which is capable of preventing TNFR activation by TNF-alpha and thus the initiation of the inflammation cascade. A "tumor necrosis factor receptor (TNFR)", or death receptor, is a cytokine receptor that binds tumor necrosis factors (e.g., TNF-alpha) (Locksley R M, et al. 2001. Cell 104 (4): 487-501). The determination of the inhibiting capacity on the TNFR activation by TNF-alpha can be detected using standard assays to measure the activation of TNFR such as the ones described by Solorzano et al. (Solorzano C. C. et al. 1998. J Appl Physiol 84: 1119-1130) or by Hyunil et al. (Hyunil Ha et al. 2009. Current Protocols in Immunology Chapter 11 Unit 11.9D).

Inhibitory antibodies, or fragments thereof, against TNF-alpha may be readily available, or may be readily produced by using conventional molecular biology techniques. By illustrative, using immunogens derived from, for example, the TNF-alpha molecule it is possible to obtain anti-protein/anti-peptide antisera or monoclonal antibodies by using standard protocols (see, for example, "Antibodies: A Laboratory Manual", ed. by Harlow and Lane (Cold Spring Harbor Press: 1988)). A mammal, such as a mouse, a hamster or rabbit can be immunized with an immunogenic form of the peptide (e.g., TNF-alpha or an antigenic fragment thereof, which is capable of eliciting an antibody response). Techniques for conferring immunogenicity on a protein or peptide, include conjugation to carriers or other techniques, are well known in the art. An immunogenic portion of a polypeptide can be administered in the presence of adjuvant. The progress of immunization can be monitored by detection of antibody titers in plasma or serum. Standard ELISA or other immunoassays can be used with the immunogen as antigen to assess the levels of antibodies. In a preferred embodiment, the antibodies forming part of the compositions of the invention are immuno-specific for antigenic determinants of TNF-alpha (or a variant at least 80%, 85%, 90%, 95%, or 98% identical thereto). In certain embodiment, the immunospecific subject antibodies do not substantially cross react with a non-vertebrate (such as yeast) TNF-alpha related protein. By "not substantially cross react" it is meant that the antibody has a binding affinity for a non-homologous protein which is at least one order of magnitude, more preferably at least 2 orders of magnitude, and even more preferably at least 3 orders of magnitude less than the binding affinity of the antibody for a TNF-alpha.

Thus, the antibody which can be used for the purposes of the instant invention as an inhibitory antibody against TNF-alpha is capable of binding to an epitope of TNF-alpha; typically, at least 6, 8, 10, or 12, contiguous amino acids are required to form an epitope, however, epitopes which involve non-contiguous amino acids may require more, e.g., at least 15, 25, or 50 amino acid. Illustrative TNF-alpha inhibitory antibodies include, for example, polyclonal antibodies, monoclonal antibodies (mAbs), Fab and scFv fragments thereof, bispecific antibodies, heteroconjugates, human and humanized antibodies, etc. Such antibodies may be produced in a variety of ways, including hybridoma cultures, recombinant expression in bacteria or mammalian cell cultures, and recombinant expression in transgenic animals. Also antibodies can be produced by selecting a sequence from a library of sequences expressed in display systems such as filamentous phage, bacterial, yeast or ribosome. There is abundant guidance in the literature for selecting a particular production methodology (see, e.g., Chadd and Chamow, Curr. Opin. Biotechnol., 12:188-194 (2001).

The inhibitory antibody against TNF-alpha is an inhibitory mAb to TNF-alpha including, but not limited to, the antibodies sold under the generic names of Infliximab (Remicade®, Johnson and Johnson; described in U.S. Pat. No. 5,656,272), Adalimumab (Humira®, Abbott Laboratories, a human anti-TNF-alpha mAb described in U.S. Pat. No. 6,090,382 as D2E7), etc., and antibodies in clinical development such as Golimumab (or CNTO 148; WO 02/12502), etc. Further examples of anti-TNF-alpha antibodies, or fragments thereof, include CDP571 (a humanized monoclonal anti-TNF-alpha IgG4 antibody), CDP 870 (a humanized monoclonal anti-TNF-alpha antibody fragment), an anti-TNF dAb (Peptech), etc.

Additional antibodies to human TNF-alpha and fragments thereof are disclosed in U.S. Pat. Nos. 6,593,458, 6,509,015, 6,498,237, 6,451,983, 6,448,380, 6,258,562, 6,090,382, 7,223,394 and U.S. patent application US 2003/0219438 A1.

In a preferred embodiment, the biological drug is an inhibitory mAb to TNF-alpha selected from the group consisting of infliximab and adalimumab.

The method of the invention allows for classifying a patient as a responder or as a non-responder patient to a treatment, said treatment comprising the administration to said patient of a biological drug selected from infliximab and adalimumab that is periodically administered by repetitive administrations, wherein said patient suffers from rheumatoid arthritis which is treatable with said biological drug under said treatment and wherein said patient has received at least one dose from said biological drug.

According to the method of the invention, the concentration of the circulating biological drug in a sample from the patient under study is determined at a time t1, wherein said time t1 corresponds to a time point within the period of time between two successive administrations of said biological drug [step a)]. This step is intended to determine the bioavailability of the biological drug administered to the patient under study.

The term "t1" corresponds to a time point within the period of time between two successive administrations of said biological drug to the patient. The period of time between two successive administrations, hereinafter referred to as "period of time ti-tj", may vary within a broad range, for example, said period of time may comprise, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or even more days; typically, 1, 2, 3, 4, 5, 6, 7, 8, 9, 10, 11, 12 or even more weeks, or 1, 2, 3, 4, 5, 6 or even more months. In a particular embodiment, t1 is a time point in the first half of said period of time ti-tj; in another particular embodiment, t1 is a time point in the second half of said period of time ti-tj; and, in another particular embodiment, t1 is a time point around the half of said period of time ti-tj. By illustrative, the period of time ti-tj may be 4 weeks and t1 may be a time point within the first half of said period of time ti-tj (e.g., day 1, 2, 3, 4, 5, 6, 7, 8, 9, 10, 11, 12, 13 or 14 after the day of the prior administration (ti)); alternatively, the period of time ti-tj may be 4 weeks and t1 may be a time point within the second half of said period of time ti-tj (e.g., day 16, 17, 18, 19, 20, 21, 22, 23, 24, 25, 26, 27 or 28 after the day of the prior administration (ti)); or alternatively, the period of time ti-tj may be 4 weeks and t1 may be a time point around the half of said period of time ti-tj (e.g., day 13, 14, 15, 16, or 17 after the day of the prior administration (ti)). In a particular embodiment, said period of time ti-tj is 4 weeks and t1 is a time point within the second half of said period of time ti-tj, i.e., within the last two weeks of said period of time ti-tj, preferably within the last week of said period of time ti-tj, more preferably 6, 5, 4 or 3 days before the day of the following administration (tj).

The precise dose to be administered to the patient will depend, among other features, on the route of administration, and the seriousness of the disease or disorder to be treated, and should be decided according to the judgment of the physician and the patient's needs. Generally, the biological drug is administered to the patient in need of treatment at a dose of approximately 0.005 mg per kilogram of body weight to approximately 50 mg per kilogram of body weight; typically the dose ranges from approximately 0.5 mg per kilogram of body weight to approximately 15 mg per kilogram of body weight. In a preferred embodiment the dose is between 3 and 5 mg/kg intravenously. In another preferred embodiment the dose is approximately 0.7 mg/kg subcutaneously.

The term "circulating biological drug" as used herein, relates to the biological drug that is present in a fluid of the patient's body (e.g., blood, serum, milk, etc.) and can be detected by using standard methods.

The biological drug of the method of the invention is an antibody. The concentration of an antibody can be determined by practically any method known by the person skilled in the art, such as, an immunoassay, for example, an ELISA (Enzyme-Linked Immunosorbent Assay), ELISA Using Slope Correction, RIA (radioimmunoassay), competitive EIA (competitive enzyme immunoassay), DAS-ELISA (double antibody sandwich-ELISA), bridging-ELISA, techniques based on the use of protein or antibody microarrays, technologies based on discrete microparticles, assays based on the precipitation of colloidal gold, affinity chromatography techniques, ligand binding assays, lectin binding assays, biosensors, etc., preferably by an immunoassay. In a particular embodiment, the concentration of the circulating antibodies (biological drug) is measured by an ELISA, as it is shown in the examples of the present invention.

In a second step [step b)], the method of the invention comprises comparing the concentration of the circulating biological drug at said t1 with a Reference Value 1 (RV1) wherein RV1 is a therapeutic efficiency cut-off value of the concentration of the circulating biological drug.

The term "therapeutic efficiency cut-off value of the concentration of the circulating biological drug" (RV1), as used herein, relates to the concentration of the biological drug that is available in the circulating blood for which no positive titer of antibody against the biological drug is measured in the same sample. The term "no positive titer" as used herein is equivalent to a value below RV2, the term "RV2" being defined below.

Further, according to the method of the invention, if the concentration of the circulating biological drug is lower than RV1, then said patient is classified as a non-responder patient to said treatment/biological drug.

On the contrary, if a t1, the concentration of the circulating biological drug is equal to, or higher than, RV1, then said patient is classified as a responder patient to said treatment/biological drug.

In a more specific embodiment, the biological drug is infliximab and RV1 is 1.5 µg/ml. In another more specific embodiment, the biological drug is adalimumab and RV1 is 0.8 µg/ml.

In a particular embodiment, the method of the invention further comprises, in addition to the determination of the concentration of said circulating biological drug (infliximab or adalimumab), the determination of the concentration of antibodies to said biological drug; thus in a particular embodiment, the method of the invention comprises the steps of:

1) determining the concentration of the circulating biological drug in a sample from said patient at a time t1 wherein said t1 corresponds to a time point within the period of time between two successive administrations of said biological drug,
2) determining the concentration of antibodies against said biological drug in a sample from said patient at a time t1; and
3) comparing the concentration of the circulating biological drug at said t1 with a Reference Value 1 (RV1) and the concentration of antibodies against said biological drug at said time t1 with a Reference Value 2 (RV2), wherein
RV1 is a therapeutic efficiency cut-off value of the concentration of the circulating biological drug; and
RV2 is the cut-off value of the concentration of said antibody against the biological drug as determined in a group of treatment-naïve individuals by the same assay as that used for determining the concentration of the antibody against the biological drug in step 2), and wherein if the concentration of the circulating biological drug is lower than RV1 and the concentration of antibodies against said biological drug is higher than RV2, then said patient is classified as a non-responder patient to said treatment, and wherein if the concentration of the circulating biological drug is equal to, or higher than, RV1 and the concentration of antibodies against said biological drug is equal to, or lower than, RV2, then said patient is classified as a responder patient to said treatment; and wherein if the biological drug is infliximab, then RV1 is 1.5 µg/ml; and wherein if the biological drug is adalimumab, then RV1 is 0.8 µg/ml.

Said particular embodiment comprises a first step 1) which is equivalent to the first step [step a)] previously described for the method of the invention. In a second step [step 2) of this particular embodiment], the method of the invention comprises determining the concentration of antibodies against said biological drug in a sample from said patient at said time t1. This step is intended to determine the immunogenicity of the biological drug administered to the patient under study. Examples 1 and 2 of the present invention show a method including said step. This step is not necessary in order to classify a patient as a responder or non-responder to a biological drug since it is sufficient to determine the levels of concentration of the circulating biological drug in a sample of said patient to obtain a good correlation with the clinical response. This is shown in Examples 3 and 4 of the present invention.

The term "antibody against a biological drug" as used herein, relates to any antibody that the immunosystem of the patient treated with said biological drug produces that binds specifically to said biological drug. Types of antibodies include IgA, IgD, IgE, IgG and IgM. The concentration of antibodies against a biological drug can be measured by any method known by the person skilled in the art, for example, an immunoassay, e.g., ELISA, ELISA Using Slope Correction, RIA, competitive EIA, DAS-ELISA, bridging-ELISA, techniques based on the use of antibody microarrays, etc., as it has been previously discussed. In a particular embodiment, the concentration of the antibodies against a biological drug is measured by an ELISA, as it is shown in the Examples 1 and 2 of the present invention.

If low amount of antibodies against a biological drug are present in the sample, these can be complexed with the biological drug, and, therefore, they would not be detected in the determination of the antibodies against the biological drug (i.e., immunogenicity determination). This is a phenomenon called "drug interference". In order to measure the antibody titer in the presence of drug-antibody complexes, complexes can be disaggregated by using, for example, an acid dissociation protocol. In a particular embodiment, the samples can be treated with an acid (e.g., acetic acid) prior to perform the immunogenicity determination, such as it is mentioned in the accompanying examples.

In the third step [step 3] of this particular embodiment], the method of the invention comprises comparing the concentration of the circulating biological drug at said t1 with a Reference Value 1 (RV1) and the concentration of antibodies against said biological drug at said time t1 with a Reference Value 2 (RV2), wherein RV1 is a therapeutic efficiency cut-off value of the concentration of the circulating biological drug, and RV2 is the cut-off value of the concentration of said antibody against the biological drug as determined in a group of treatment-naïve individuals by the same assay as that used for determining the concentration of the antibody against the biological drug in step b) of said particular embodiment).

The term "therapeutic efficiency cut-off value of the concentration of the circulating biological drug" (RV1), as defined above, relates to the concentration of the biological drug that is available in the circulating blood for which no positive titer of antibody against the biological drug is measured in the same sample. The term "no positive titer" as used herein is equivalent to a value below RV2, the term "RV2" being defined below, i.e., the cut-off value of the immunogenicity determination as determined in a group of treatment-naïve individuals by the same assay as that used for determining the concentration of the antibody against the biological drug in step 2) [i.e., if the concentration of antibodies against said biological drug is measured by a conventional ELISA assay in step 2), the concentration of antibodies against said biological in the group of treatment-naïve individuals is also determined under the same conditions by using the same conventional ELISA assay]. In order to generate RV1, ideally the concentrations of the circulating biological drug in a group of patients treated with the biological drug are used. Preferably at least 2, more preferably 2, 3, 10, 20, 40, 100 or even more patients are used.

In a more specific embodiment, the biological drug is infliximab and RV1 is 1.5 µg/ml. In another more specific embodiment, the biological drug is adalimumab and RV1 is 0.8 µg/ml.

The term "cut-off value of the concentration of said antibody against the biological drug as determined in a group of treatment-naïve individuals by the same assay as that used for determining the concentration of the antibody against the biological drug in step 2)" (RV2) is understood in the present invention the value that defines the background measurements of the assay used for determining the concentration of the antibody against the biological drug in step 2), what means, that above said value, the measurements are true positive values since are above the background or noise threshold of the method used.

The term "treatment-naïve individuals" as used herein, relates to subjects who are new (naïve) to the biological drug therapy, that is, that were never treated before with said therapy. Thus, those subjects should not present antibodies against the biological drug and thus the concentration measured in a group of said subjects could be used to determine the cut-off value of the immunogenicity determination. The group of naïve subjects is preferably formed by more than 1, preferably 2 or more, more preferably 3 or more, most preferably 4, 10, 20, 30, 40, 50, 60, 70, 80, 90, 100, 500, or even more treatment-naïve individuals. The cut off-value is then calculated as the mean of the values obtained from each of the treatment-naïve individuals.

In a particular embodiment, the immunoassay is an ELISA. In a more specific embodiment, the immunoassay is an ELISA, the biological drug is infliximab and RV2 is 150 ng/ml. In another more specific embodiment, the immunoassay is an ELISA, the biological drug is adalimumab and RV2 is 32 ng/ml.

Further, according to said particular embodiment of the method of the invention, if the concentration of the circulating biological drug is lower than RV1 and the concentration of antibodies against said biological drug is higher than RV2, then said patient is classified as a non-responder patient to said treatment/biological drug.

On the contrary, if a t1, the concentration of the circulating biological drug is equal to, or higher than, RV1 and the concentration of antibodies against said biological drug is equal to, or lower than, RV2, then said patient is classified as a responder patient to said treatment/biological drug.

The term "responder patient" as used herein, relates to patients for which the predicted response to the treatment/biological drug is positive. Similarly, the term "non-responder patient" as used herein, relates to patients for which the predicted response to the treatment/biological drug is negative.

The term "predicted response" or similar, as used herein refers to the determination of the likelihood that the patient will respond either favorably or unfavorably to a given therapy/biological drug. Especially, the term "prediction", as used herein, relates to an individual assessment of any parameter that can be useful in determining the evolution of a patient. As it will be understood by those skilled in the art, the prediction of the clinical response to the treatment with a biological drug, although preferred to be, need not be correct for 100% of the subjects to be diagnosed or evaluated. The term, however, requires that a statistically significant portion of subjects can be identified as having an increased probability of having a positive response. Whether a subject is statistically significant can be determined without further effort by the person skilled in the art using various well known statistic evaluation tools, e.g., determination of confidence intervals, p-value determination, Student's t-test, Mann-Whitney test, etc. Details are found in Dowdy and Wearden, Statistics for Research, John Wiley & Sons, New York 1983. Preferred confidence intervals are at least 50%, at least 60%, at least 70%, at least 80%, at least 90% at least 95%. The p-values are, preferably, 0.2, 0.1 or 0.05.

The term "clinical response", as used herein, refers to the response to a biological drug of the subject suffering from a pathology which is treatable with said biological. Standard criteria may vary from disease to disease.

Patients achieving complete or partial response are considered "responders", and all other patients are considered "non-responders".

The response in individual patients may be characterized as a complete response, a partial response, stable disease, and progressive disease, as these terms are understood in the art. Thus, the method of the invention allows for classifying a patient as a responder or as a non-responder patient to a treatment, said treatment comprising the administration to said patient of a biological drug selected from the group consisting of infliximab and adalimumab that is periodically administered by repetitive administrations, wherein said patient suffers from rheumatoid arthritis which is treatable with said biological drug under said treatment and wherein said patient has received at least one dose from said biological drug.

In the case of rheumatoid arthritis, the standard used is the Disease Activity Score determination (DAS28, see table 1). DAS28 is determined according to the European League against Rheumatism (EULAR) (Aletaha D, et al. 2010. Ann. Rheum. Dis. 69 (9): 1580-8).

In a more particular embodiment, the biological drug is infliximab. Infliximab is a mAb anti-TNF-alpha which can be used for the treatment of, for example, psoriasis, Crohn's disease, ankylosing spondylitis, psoriatic arthritis, rheumatoid arthritis and ulcerative colitis. In another particular embodiment the biological drug is adalimumab. Adalimumab is a TNF-alpha inhibitor which can be used for the treatment of, for example, rheumatoid arthritis, psoriatic arthritis, ankylosing spondylitis, Crohn's disease, moderate to severe chronic psoriasis and juvenile idiopathic arthritis. In a specific embodiment, said pathology of the patient to be treated by a biological drug is rheumatoid arthritis and said biological drug is infliximab, RV1 is 1.5 µg/ml and RV2 is 150 ng/ml (as determined by ELISA).

In another specific embodiment, said pathology of the patient to be treated by a biological drug is rheumatoid arthritis and said biological drug is adalimumab, RV1 is 0.8 µg/ml and RV2 is 32 ng/ml (as determined by ELISA).

The following examples illustrate the invention and should not be considered as limitative of the scope thereof.

EXAMPLES

The following methods were common to all the Examples (as applicable).

Methods

Sampling

Blood samples from patients (Examples 1 and 2) were collected before each infusion, and serum was obtained, aliquoted and stored at −20° C.

Analysis

An aliquot of each serum was defrozen. All sera were tested simultaneously for free biological drug concentration (bioavailability) and anti-biological drug antibodies (immunogenicity).

Bioavailability Analysis

An immunoassay was designed to specifically measure the concentration of the free biological drug (antibodies to human TNF-alpha infliximab or adalimumab) in the sera of patients. Briefly, a 96-well ELISA plate was coated with human recombinant TNF-alpha, whose amino acid sequence is shown in SEQ ID NO: 2, via a murine anti-TNF-alpha monoclonal antibody. Recombinant human TNF-alpha was obtained in *Escherichia coli*, by cloning into an expression vector. The protein was expressed as a fusion protein bearing a six histidine tag in its amino terminus and purified by affinity chromatography.

Sera were incubated in the plate in different serial dilutions and replicas. If the biological drug is present in the serum of the patient, it will bind to the fixed TNF-alpha. Detection of the bound biological drug takes place with a biotinylated monoclonal antibody to said biological drug (infliximab or adalimumab). After washing, the amount of bound biotinylated antibody can be measured by incubating with streptavidin-polyHRP (Fitzgerald Industries Limited), and after another washing step incubating with 3,3′,5,5′-tetramethylbenzidine (TMB), the substrate for horseradish peroxidase (HRP). If the result is positive a blue color will appear. The reaction is stopped with HCl, which changes the blue color into yellow. This yellow color can be measured in an ELISA reader at 450 nm. In parallel, a calibration standard curve is constructed using pure biological drug. This correlates the concentration of the biological drug to a given absorbance intensity. The concentration of free biological drug in the serum of each patient is obtained in micrograms per milliliter (µg/ml) of serum by extrapolation of the absorbance intensity in the calibration curve.

Immunogenicity Standard Analysis

A bridging immunoassay was designed to specifically measure the concentration of the immunoglobulins against the biological drug in the sera of patients. Briefly, a 96-well ELISA plate is coated with the biological drug. Sera are incubated in the plate in different serial dilutions and replicas. If anti-biological drug antibodies are present in the serum of the patient, they will bind to the fixed biological drug. Finally, biotinylated biological drug is added as a detection reagent. If anti-biological drug antibodies are present in the serum of the patient, the biotinylated biological drug will bind to them. After washing, the amount of anti-biological drug antibodies can be measured by incubating with streptavidin-polyHRP, and after another washing step incubating with TMB, the substrate for HRP. If the result is positive a blue color will appear. The reaction is stopped with HCl, which changes the blue color into yellow. This yellow color can be measured in an ELISA reader at 450 nm. In parallel, a calibration standard curve is constructed using serial dilutions of a serum sample with known concentration of anti-biological drug antibodies as a positive control. This correlates the concentration of the antibodies to a given absorbance intensity. The concentration of antibodies in the serum of each patient is obtained in arbitrary units per milliliter (AU/ml) of serum by extrapolation of the absorbance intensity in the calibration curve. For quantification purposes, in the case of infliximab, 1 AU/ml corresponds to 10 ng/ml of anti-infliximab antibodies, and, in the case of adalimumab, 1 AU/ml corresponds to 4 ng/ml of anti-adalimumab antibodies.

Immunogenicity Analysis with Acid Dissociation Protocol

If low amount of anti-biological drug antibodies are present in the sample, these can be complexed with the biological drug, and, therefore, they would not be detected in the immunogenicity analysis. This is a phenomenon called "drug interference". In order to measure the antibody titer in the presence of biological drug-antibody complexes, complexes were disaggregated using an acid dissociation protocol. The samples were treated with acetic acid prior to the analysis, and the immunogenicity analysis was carried out as explained before.

Disease Activity Score Determination (DAS28)

Disease Activity Score was determined by the rheumatologist according to the European League against Rheumatism (EULAR) criteria for every patient at each sampling point (Table 1). A high value of DAS28 indicates the progression of the disease. A low value of DAS28 indicates the remission of the disease.

TABLE 1

DAS28 cut-off values according to EULAR

| Status of disease | DAS28 ranges |
|---|---|
| Remission | <1.6 |
| Low activity | <2.4 |
| Moderate activity | 2.4 ≤ DAS28 ≤ 3.7 |
| High activity | >3.7 |

Classification of clinical response. In rheumatoid arthritis patients, clinical response to the biological drug treatment was assessed according to DAS28 index. Definition of responder and non-responder was assessed one year after the initiation of the treatment with the corresponding drug.

According to EULAR:

patients were grouped as responders if:

$$\Delta DAS28 = DAS28_{predose} - DAS28_{1\ year} \geq 1.2;\ and$$

patients were grouped as non-responders if:

$$\Delta DAS28 = DAS28_{predose} - DAS28_{1\ year} < 1.2$$

Bioavailability and Immunogenicity Cut-off Values Determination

Pre-dose samples of 52 patients (infliximab) and 10 patients (adalimumab) were analysed in order to calculate the cut-off value of both the concentration of the biological drug (bioavailability cut-off) and the concentration of anti-biological drug antibodies (immunogenicity cut-off), which were defined as the average of the background signals of all the pre-dose sera plus 1.645 times the standard deviation of all the values.

Bioavailability and Immunogenicity Reference Values Determination

A reference value 1 (RV1) corresponds to the therapeutic efficiency threshold for each of the circulating biological drugs as detailed in the "Determination of the diagnostic cut-offs" sections for infliximab and adalimumab as shown in Examples 1 and 2. A reference value 2 (RV2) corresponds to the lowest positive titer of antibodies against each biological drug that can be quantified (expressed in units (U) or ng (nanograms) per milliliter) as detailed in the "Determination of the diagnostic cut-offs" sections for infliximab and adalimumab as shown in Examples 1 and 2.

Statistical Analysis

SigmaPlot v11.0 and SPSS v11.0 were used for data analysis. Samples did not follow a normal distribution according to Kolmogorov-Smirnov and Shapiro-Wilk tests. Therefore non-parametric tests were used for the subsequent analysis. Kendall's Tau and Spearman's Rho were used to study the correlation between variables. P values less than 0.05 were considered as statistically significant.

Example 1

Correlation of Bioavailability and Immunogenicity of Infliximab with the Clinical Response of Patients Suffering from Rheumatoid Arthritis Subjects: Rheumatoid arthritis (RA) patients, 75, fulfilling the criteria of the American College of Rheumatology (ACR) of 1987 (1987 ACR criteria) [Arnett F. et al. (1988). "The American Rheumatism Association 1987 revised criteria for the classification of rheumatoid arthritis". *Arthritis Rheum.* 31 (3): 315-24] and about to start treatment with infliximab, were enrolled consecutively. A total of 612 serum samples from said 75 patients suffering from RA were analysed.

Treatment: Patients received doses of 3 mg/kg of infliximab (Remicade®) intravenously. The frequency of drug administration was as follows: first infusion on the first day of treatment (baseline), second infusion two weeks later, third infusion one month after the second, fourth infusion two months after the third, and subsequent infusions at eight weeks interval.

Evaluation of the patient clinical response: Disease Activity Score 28 (DAS28) was used to evaluate the clinical response of the patient according scores in Table 1. DAS28 is a validated method according to the European League against Rheumatism (EULAR) criteria. One year clinical response was determined as explained before.

Determination of bioavailability and immunogenicity of infliximab: Table 2 summarizes the average values of bioavailability and immunogenicity of infliximab.

TABLE 2

Average of infliximab bioavailability and immunogenicity. SD: standard deviation; Cmin: minimum concentration; Cmax: maximum concentration.

| | Infliximab bioavailability (µg/ml) | | | | Immunogenicity (antibodies against infliximab) (AU/ml) | | | |
|---|---|---|---|---|---|---|---|---|
| Samples | Average | SD | Cmin | Cmax | Average | SD | Cmin | Cmax |
| 612 | 4.27 | 7.39 | 0.002 | 54.4 | 437.47 | 2490.69 | 1.000 | 45904.64 |

Further, Table 3 summarizes the average values of infliximab bioavailability and immunogenicity as a function of the treatment.

TABLE 3

Average of infliximab bioavailability and immunogenicity as a function of the treatment. SD: standard deviation; Cmin: minimum concentration; Cmax: maximum concentration; N, number of patients.

| Infusion number | Infliximab bioavailability (µg/ml) | | | | | Immunogenicity (antibodies against infliximab) (AU/ml) | | | | |
|---|---|---|---|---|---|---|---|---|---|---|
| | Average | SD | Cmin | Cmax | N | Average | SD | Cmin | Cmax | N |
| 0 | 0.002 | 0.000 | 0.002 | 0.002 | 35 | 1.00 | 0.00 | 1.00 | 1.00 | 35 |
| 1 | 23.17 | 9.67 | 5.05 | 48.59 | 36 | 1.00 | 0.00 | 1.00 | 1.00 | 36 |
| 2 | 11.31 | 9.34 | 0.002 | 38.99 | 37 | 1.91 | 3.30 | 1.00 | 15.00 | 37 |
| 3 | 2.87 | 3.95 | 0.002 | 14.87 | 34 | 42.50 | 130.26 | 1.00 | 718.92 | 34 |
| 4 | 1.58 | 2.57 | 0.002 | 11.88 | 29 | 200.68 | 477.53 | 1.00 | 1665.90 | 29 |
| 5 | 1.82 | 3.41 | 0.002 | 13.52 | 25 | 479.24 | 1705.36 | 1.00 | 8458.88 | 25 |
| 6 | 2.61 | 3.78 | 0.002 | 13.13 | 22 | 460.31 | 1226.83 | 1.00 | 4606.24 | 22 |

TABLE 3-continued

Average of infliximab bioavailability and immunogenicity as a function of the treatment.
SD: standard deviation; Cmin: minimum concentration; Cmax: maximum concentration;
N, number of patients.

| Infusion number | Infliximab bioavailability (µg/ml) | | | | | Immunogenicity (antibodies against infliximab) (AU/ml) | | | | |
|---|---|---|---|---|---|---|---|---|---|---|
| | Average | SD | Cmin | Cmax | N | Average | SD | Cmin | Cmax | N |
| 7 | 2.61 | 4.00 | 0.002 | 15.40 | 18 | 791.14 | 2324.35 | 1.00 | 9607.56 | 18 |
| 8 | 3.56 | 4.81 | 0.002 | 14.35 | 14 | 1516.52 | 5666.53 | 1.00 | 21204.28 | 14 |

Tables 4-6 provide individual values of infliximab bioavailability and immunogenicity as a function of the treatment for each patient.

TABLE 4

Individual values of circulating infliximab (IFX) and immunogenicity (antibodies). Infusion numbers 0 to 3 are shown.

| | Infusion number 0 | | | Infusion number 1 | | | Infusion number 2 | | | Infusion number 3 | |
|---|---|---|---|---|---|---|---|---|---|---|---|
| Patient | IFX (µg/ml) | Antibodies (AU/ml) | Patient | IFX (µg/ml) | Antibodies (AU/ml) | Patient | IFX (µg/ml) | Antibodies (AU/ml) | Patient | IFX (µg/ml) | Antibodies (AU/ml) |
| 1 | 0.002 | 1.000 | 1 | 21.514 | 1.000 | 1 | 3.966 | 1.000 | 4 | 0.002 | 15.000 |
| 5 | 0.002 | 1.000 | 4 | 24.828 | 1.000 | 4 | 6.414 | 1.000 | 7 | 1.529 | 1.000 |
| 6 | 0.002 | 1.000 | 5 | 30.143 | 1.000 | 5 | 19.442 | 1.000 | 8 | 4.278 | 1.000 |
| 7 | 0.002 | 1.000 | 6 | 5.331 | 1.000 | 6 | 3.317 | 1.000 | | | |
| 8 | 0.002 | 1.000 | 7 | 29.050 | 1.000 | 7 | 8.713 | 1.000 | 14 | 0.002 | 718.918 |
| 12 | 0.002 | 1.000 | 8 | 30.607 | 1.000 | 8 | 13.349 | 1.000 | 17 | 0.002 | 1.000 |
| 16 | 0.002 | 1.000 | 12 | 48.589 | 1.000 | 12 | 27.184 | 1.000 | 18 | 3.830 | 1.000 |
| 17 | 0.002 | 1.000 | 14 | 22.375 | 1.000 | 14 | 0.002 | 1.000 | 19 | 0.002 | 209.533 |
| 18 | 0.002 | 1.000 | 16 | 19.727 | 1.000 | 16 | 15.343 | 1.000 | 20 | 0.002 | 1.000 |
| 19 | 0.002 | 1.000 | 17 | 30.149 | 1.000 | 17 | 0.461 | 1.000 | 21 | 14.059 | 1.000 |
| 20 | 0.002 | 1.000 | 19 | 5.046 | 1.000 | 18 | 9.170 | 1.000 | 23 | 0.002 | 15.000 |
| 21 | 0.002 | 1.000 | 20 | 20.684 | 1.000 | 19 | 0.002 | 6.585 | 24 | 3.187 | 1.000 |
| 22 | 0.002 | 1.000 | 23 | 30.993 | 1.000 | 20 | 4.987 | 1.000 | 27 | 2.192 | 1.000 |
| 23 | 0.002 | 1.000 | 24 | 26.668 | 1.000 | 21 | 38.988 | 1.000 | 29 | 3.331 | 1.000 |
| 24 | 0.002 | 1.000 | 27 | 37.440 | 1.000 | 23 | 6.196 | 1.000 | 31 | 0.002 | 15.000 |
| 27 | 0.002 | 1.000 | 29 | 37.448 | 1.000 | 24 | 17.797 | 1.000 | 33 | 4.742 | 1.000 |
| 29 | 0.002 | 1.000 | 31 | 23.707 | 1.000 | 27 | 13.983 | 1.000 | 35 | 0.002 | 99.345 |
| 31 | 0.002 | 1.000 | 33 | 34.567 | 1.000 | 29 | 26.635 | 1.000 | 44 | 0.002 | 15.000 |
| 33 | 0.002 | 1.000 | 35 | 11.389 | 1.000 | 31 | 0.310 | 1.000 | 60 | 0.002 | 15.000 |
| 35 | 0.002 | 1.000 | 37 | 15.527 | 1.000 | 33 | 15.530 | 1.000 | 66 | 1.084 | 1.000 |
| 37 | 0.002 | 1.000 | 44 | 14.028 | 1.000 | 35 | 0.002 | 15.000 | 68 | 10.586 | 1.000 |
| 44 | 0.002 | 1.000 | 66 | 33.058 | 1.000 | 37 | 15.689 | 1.000 | 71 | 3.045 | 1.000 |
| 66 | 0.002 | 1.000 | 71 | 34.340 | 1.000 | 44 | 1.702 | 1.000 | 87 | 1.064 | 1.000 |
| 71 | 0.002 | 1.000 | 87 | 27.373 | 1.000 | 66 | 15.629 | 1.000 | 91 | 0.002 | 209.960 |
| 87 | 0.002 | 1.000 | 91 | 12.255 | 1.000 | 71 | 28.048 | 1.000 | 95 | 0.212 | 1.000 |
| 91 | 0.002 | 1.000 | 95 | 16.452 | 1.000 | 87 | 11.475 | 1.000 | 110 | 14.867 | 1.000 |
| 110 | 0.002 | 1.000 | 110 | 26.161 | 1.000 | 91 | 0.002 | 15.000 | 125 | 4.984 | 1.000 |
| 125 | 0.002 | 1.000 | 125 | 17.282 | 1.000 | 95 | 8.843 | 1.000 | 137 | 0.002 | 33.923 |
| 137 | 0.002 | 1.000 | 137 | 30.077 | 1.000 | 125 | 18.549 | 1.000 | 138 | 8.768 | 1.000 |
| 138 | 0.002 | 1.000 | 138 | 16.817 | 1.000 | 137 | 12.262 | 1.000 | 151 | 5.334 | 1.000 |
| 151 | 0.002 | 1.000 | 151 | 14.821 | 1.000 | 138 | 13.075 | 1.000 | 157 | 4.634 | 1.000 |
| 157 | 0.002 | 1.000 | 157 | 18.985 | 1.000 | 151 | 18.129 | 1.000 | 168 | 0.002 | 11.185 |
| 172 | 0.002 | 1.000 | 168 | 10.657 | 1.000 | 157 | 19.052 | 1.000 | 172 | 3.128 | 1.000 |
| 177 | 0.002 | 1.000 | 172 | 17.258 | 1.000 | 168 | 2.105 | 1.000 | 177 | 0.002 | 65.310 |
| 179 | 0.002 | 1.000 | 177 | 15.448 | 1.000 | 172 | 10.360 | 1.000 | 179 | 2.775 | 1.000 |
| | | | 179 | 23.144 | 1.000 | 177 | 1.433 | 1.000 | | | |
| | | | | | | 179 | 10.228 | 1.000 | | | |

TABLE 5

Individual values of circulating infliximab (IFX) and immunogenicity (antibodies). Infusion numbers 4 to 7 are shown.

| Infusion number 4 | | | Infusion number 5 | | | Infusion number 6 | | | Infusion number 7 | | |
|---|---|---|---|---|---|---|---|---|---|---|---|
| Patient | IFX (µg/ml) | Antibodies (AU/ml) | Patient | IFX (µg/ml) | Antibodies (AU/ml) | Patient | IFX (µg/ml) | Antibodies (AU/ml) | Patient | IFX (µg/ml) | Antibodies (AU/ml) |
| 4 | 0.002 | 112.763 | 7 | 0.002 | 13.645 | 7 | 0.002 | 14.555 | 8 | 1.457 | 1.000 |
| 6 | 0.002 | 31.175 | 8 | 6.421 | 1.000 | 8 | 0.384 | 1.000 | 19 | 0.002 | 9607.560 |
| 7 | 0.040 | 1.000 | 18 | 0.002 | 1.000 | 19 | 0.002 | 4606.240 | 27 | 0.002 | 1.000 |
| 8 | 1.233 | 1.000 | 19 | 0.002 | 1676.180 | 27 | 0.002 | 35.580 | 29 | 2.255 | 1.000 |
| 14 | 0.002 | 1559.520 | 27 | 0.930 | 1.000 | 31 | 0.002 | 935.160 | 31 | 0.002 | 1352.732 |
| 17 | 0.002 | 200.373 | 29 | 0.807 | 1.000 | 33 | 12.269 | 1.000 | 33 | 8.662 | 1.000 |
| 18 | 4.579 | 1.000 | 31 | 0.002 | 297.668 | 44 | 0.002 | 15.000 | 44 | 0.002 | 15.000 |
| 19 | 0.002 | 1450.960 | 33 | 13.520 | 1.000 | 60 | 2.688 | 1.000 | 60 | 0.040 | 1.000 |
| 21 | 6.254 | 1.000 | 35 | 0.002 | 15.000 | 65 | 1.879 | 1.000 | 65 | 2.664 | 1.000 |
| 23 | 0.002 | 1.000 | 37 | 0.002 | 992.080 | 66 | 2.160 | 1.000 | 66 | 3.117 | 1.000 |
| 24 | 2.191 | 1.000 | 44 | 0.002 | 281.540 | 68 | 13.129 | 1.000 | 68 | 15.403 | 1.000 |
| 27 | 1.022 | 1.000 | 60 | 0.040 | 1.000 | 71 | 6.121 | 1.000 | 91 | 0.002 | 2985.120 |
| 29 | 0.731 | 1.000 | 66 | 0.911 | 1.000 | 87 | 0.954 | 1.000 | 95 | 0.002 | 15.000 |
| 31 | 0.002 | 117.420 | 68 | 9.977 | 1.000 | 91 | 0.002 | 3675.520 | 110 | 3.451 | 1.000 |
| 33 | 2.567 | 1.000 | 71 | 3.388 | 1.000 | 95 | 0.002 | 1.000 | 125 | 2.805 | 1.000 |
| 37 | 0.002 | 264.788 | 87 | 0.002 | 1.000 | 110 | 5.709 | 1.000 | 139 | 6.230 | 1.000 |
| 44 | 0.002 | 1665.900 | 91 | 0.002 | 8458.880 | 125 | 3.564 | 1.000 | 168 | 0.002 | 253.072 |
| 45 | 0.040 | 1.000 | 95 | 0.002 | 82.568 | 137 | 0.002 | 15.000 | 172 | 1.037 | 1.000 |
| 66 | 1.122 | 1.000 | 110 | 3.515 | 1.000 | 139 | 2.533 | 1.000 | | | |
| 68 | 11.877 | 1.000 | 125 | 2.875 | 1.000 | 157 | 3.114 | 1.000 | | | |
| 71 | 3.647 | 1.000 | 137 | 0.002 | 15.655 | 168 | 0.002 | 815.853 | | | |
| 87 | 1.229 | 1.000 | 139 | 0.332 | 1.000 | 172 | 2.956 | 1.000 | | | |
| 91 | 0.002 | 306.800 | 157 | 2.047 | 1.000 | | | | | | |
| 95 | 0.119 | 1.000 | 168 | 0.002 | 132.660 | | | | | | |
| 110 | 2.735 | 1.000 | 172 | 0.807 | 1.000 | | | | | | |
| 125 | 1.485 | 1.000 | | | | | | | | | |
| 157 | 3.796 | 1.000 | | | | | | | | | |
| 168 | 0.002 | 91.153 | | | | | | | | | |
| 172 | 1.085 | 1.000 | | | | | | | | | |

TABLE 6

Individual values of circulating infliximab (IFX) and immunogenicity (antibodies). Infusion number 8 is shown.
Infusion number 8

| Patient | IFX (µg/ml) | Antibodies (AU/ml) |
|---|---|---|
| 19 | 0.002 | 21204.280 |
| 27 | 0.298 | 1.000 |
| 29 | 2.057 | 1.000 |
| 33 | 14.348 | 1.000 |
| 44 | 0.002 | 15.000 |
| 54 | 0.298 | 1.000 |
| 60 | 5.181 | 1.000 |
| 65 | 6.815 | 1.000 |
| 66 | 1.861 | 1.000 |
| 68 | 13.291 | 1.000 |
| 95 | 0.426 | 1.000 |
| 110 | 1.780 | 1.000 |
| 139 | 3.466 | 1.000 |
| 168 | 0.040 | 1.000 |

After the analysis of the samples the following distribution was observed for infliximab (Table 7).

TABLE 7

Distribution of patients according to different combinations of infliximab bioavailability and immunogenicity.

| Bioavailability/Immunogenicity | Patients* | Samples |
|---|---|---|
| positive/negative | 68 | 390 |
| negative/positive | 35 | 142 |
| negative/negative | 51 | 80 |
| positive/positive | 0 | 0 |

*Due to multiple number of samples per patient, patients can be present in more than one group.

FIG. 1 shows the average bioavailability and immunogenicity profiles over one year of treatment of all the patients that do not respond to the treatment with infliximab. In this example it is shown that ΔDAS28 is lower than 1.2; therefore, the patients are classified as non-responders to the treatment with infliximab. Concomitantly with the presence of antibodies against infliximab, the concentration of free infliximab drops below the cut-off value.

Figure 2:
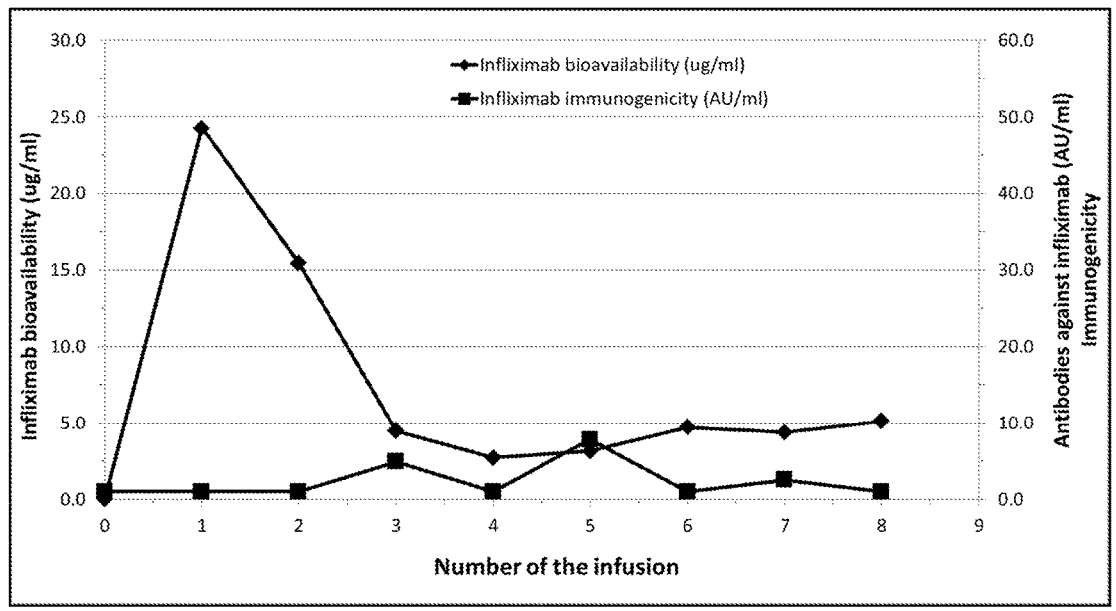
FIG. 2. Infliximab bioavailability and immunogenicity profiles over one year of treatment (top). The average values are shown for the group of patients showing response to infliximab. ΔDAS28 is indicated for each infusion time (bottom). ΔDAS28 does not increase over the year of treatment (bottom). The horizontal line in the bottom panel indicates the ΔDAS28=1.2 threshold.
Figure 2:
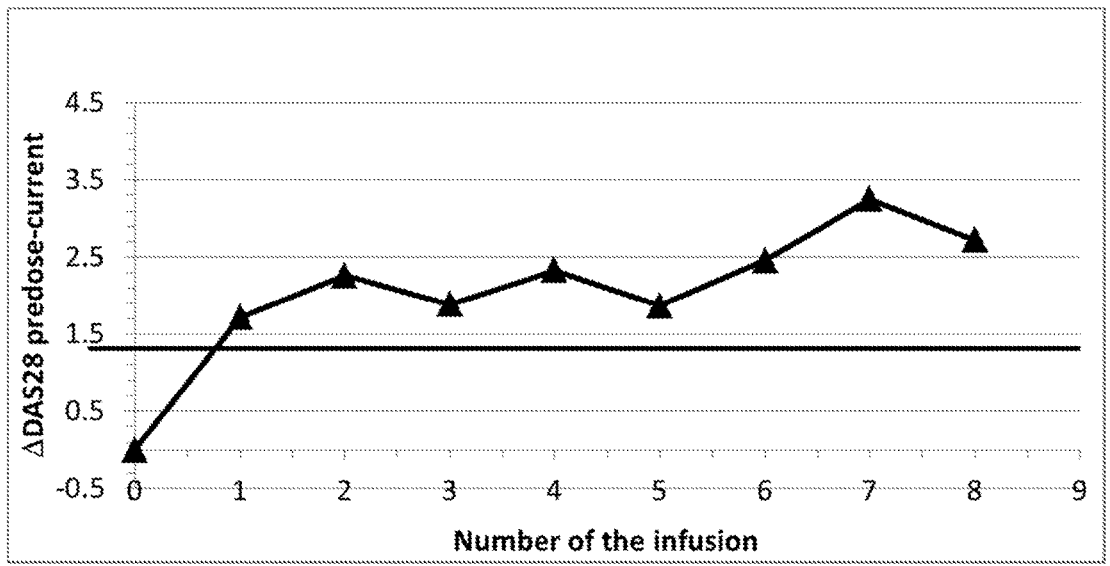

FIG. 2 shows the average bioavailability and immunogenicity profiles over one year of treatment of the patients that respond to the treatment with infliximab. In this example it is shown that ΔDAS28 is higher than 1.2; therefore, the patient is classified as responder to infliximab treatment. Concomitantly with the presence of antibodies against infliximab, the concentration of free infliximab drops below the cut-off value.

Bioavailability and immunogenicity correlation: Bioavailability and immunogenicity of infliximab strongly correlate ($p<0.01$). Statistical correlation analysis was performed using Kendall's Tau-b and Sperman tests. Correlation results are shown in Table 8.

TABLE 8

Correlation between bioavailability and immunogenicity of infliximab.

|  | Kendall's Tau-b test | | Sperman test | |
|---|---|---|---|---|
| Parameter | Correlation coefficient | p-value | Correlation coefficient | p-value |
| Bioavailability Immunogenicity | −0.491 | 1.00E−06 | −0.606 | 1.00E−06 |

Clinical correlations: The correlations between bioavailability, immunogenicity and the disease activity based on the DAS28 values were analyzed. Clinical responses strongly correlate with the levels of free infliximab (drug bioavailability) and the formation of anti-infliximab antibodies (drug immunogenicity) (Table 9). In addition, infliximab concentration and antibodies against the drug strongly correlate ($p<-0.001$). The concentration of infliximab inversely correlates with DAS28 ($p<-0.001$), whereas the concentration of anti-infliximab antibodies directly correlates with DAS28 ($p<0.001$).

TABLE 9

Correlation between the infliximab bioavailability, anti-infliximab antibodies (immunogenicity) and DAS28. A positive p value indicates a direct correlation. A negative p value indicates an inverse correlation. p values <0.05 or <−0.05 are statistically significant.

|  | Concentration of infliximab (μg/ml) (Bioavailability) | Concentration of anti-infliximab antibodies (AU/ml) (Immunogenicity) | DAS28 |
|---|---|---|---|
| Concentration of infliximab (μg/ml) | — | p < −0.001 | p < −0.001 |
| Concentration of anti-infliximab antibodies (AU/ml) | p < −0.001 | — | p < 0.001 |
| DAS28 | p < −0.001 | p < 0.001 | — |

Determination of diagnostic cut-offs: According to the standard protocol to determine immunogenicity, there is never a positive titer of anti-infliximab antibodies above 1.5 μg/ml of free infliximab. Therefore, diagnostic cut-off was determined by measuring the anti-infliximab antibodies concentration with the acid dissociation protocol in those samples with concentrations of free infliximab below 1.5 μg/ml. 45 patients (183 samples) fulfilling this criteria were analysed. 51% of the patients (33% of the samples) showed a positive immunogenicity titer (Table 10).

TABLE 10

Detection of antibodies anti-infliximab using the acid dissociation protocol in samples with free infliximab below 1.5 μg/ml.

| Samples # | Patients # | Positive samples after acid dissociation protocol/patients |
|---|---|---|
| 183 | 45 | 60 (33%)/23 |

It was further studied if there is a relationship between the level of free infliximab below 1.5 μg/ml and the presence of antibodies anti-infliximab above 15 AU/ml (equivalent to 150 ng/ml of antibodies) (limit of detection) with DAS28 (Table 11) in the whole cohort of patients.

TABLE 11

Disease activity as a function of bioavailability and immunogenicity cut-offs.

| Grouping | Average DAS28 | SD | p-value |
|---|---|---|---|
| Infliximab >1.5 μg/ml AND antibodies anti-infliximab <15 AU/ml | 3.35 | 0.97 | <0.01 |
| Infliximab <1.5 μg/ml AND antibodies anti-infliximab >15 AU/ml | 3.89 | 1.41 | |

SD, standard deviation.
p value <0.05 is statistically significant.

Inventors studied the same relationship between responder and non-responder patients (Table 12).

TABLE 12

Correlation of infliximab bioavailability and immunogenicity cut-offs with the clinical response.

| Population | Cut-offs combination | Average DAS28 (N) | SD | p-value |
|---|---|---|---|---|
| With clinical response | Free infliximab >1.5 μg/ml AND antibodies anti-infliximab <15 AU/ml | 3.30 (107) | 0.98 | 0.546 |
| | Free infliximab <1.5 μg/ml AND antibodies anti-infliximab >15 AU/ml | 3.51 (41) | 1.28 | |
| With no clinical response | Free infliximab >1.5 μg/ml AND antibodies anti-infliximab <15 AU/ml | 3.52 (33) | 0.97 | <0.01 |
| | Free infliximab <1.5 μg/ml AND antibodies anti-infliximab >15 AU/ml | 4.25 (42) | 1.46 | |

SD, standard deviation.
Different combinations of cut-offs are considered.
p values <0.05 are statistically significant.

It is demonstrated that patients with an infliximab bioavailability lower than 1.5 μg/ml and antibodies anti-infliximab higher than 15 AU/ml show a higher DAS28 than those patients with infliximab bioavailability higher than 1.5 μg/ml.

Therefore, if a patient shows a combination of free infliximab lower than (<) 1.5 μg/ml AND antibodies anti-infliximab higher than (>) 15 AU/ml, there is a higher probability that the individual is a non-responder to the infliximab treatment, showing a high activity of the disease (see EULAR guidelines on Table 1).

Figure 3:
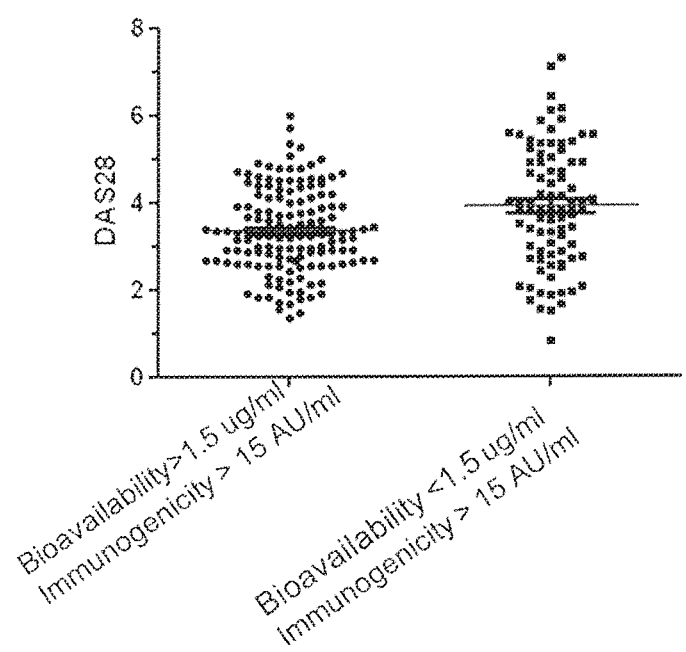
FIG. 3. DAS28 as a function of bioavailability (infliximab concentration) and immunogenicity (antibody against infliximab) variables.

FIG. 3 shows how the bioavailability of infliximab (circulating concentration of infliximab) and immunogenicity of infliximab (anti-infliximab antibodies) variables are associated to the DAS28 index, and therefore can be used to classify patients and predict the status of a patient according to the EULAR DAS guidelines.

Accordingly, a patient showing a combination of free infliximab equal to or higher than (≥) 1.5 μg/ml AND antibodies anti-infliximab equal to or lower than (≤) 15 AU/ml has a higher probability of being a responder patient to the infliximab treatment; however, patients showing bioavailability lower than 1.5 μg/ml and antibodies anti-infliximab higher than 15 AU/ml have a higher probability of being non-responder patients to the infliximab treatment.

Infliximab decision algorithm: It is demonstrated that the clinical response to infliximab closely follows the drug levels and the presence of antibodies directed against the drug.

It is thus demonstrated that if a patient has a bioavailability value below 1.5 µg/ml AND an immunogenicity value above 15 AU/ml, this will correlate with no clinical response to the treatment, therefore an increased DAS28 value (moderate or high disease activity) compared to those with bioavailability values above 1.5 µg/ml (p<0.001).

None of the analysed patients showed anti-infliximab antibodies if the concentration of free infliximab was above 1.5 µg/ml.

The following decision algorithm can be constructed from the data:

| 1. Analysis | Free infliximab bioavailability determination AND anti-infliximab antibodies analysis | |
|---|---|---|
| 2. Result | Free infliximab concentration ≥1.5 µg/ml AND anti-infliximab antibodies ≤15 AU/ml | Free infliximab concentration <1.5 µg/ml AND anti-infliximab antibodies >15 AU/ml |
| 3. Patient classification | Responder | Non-responder |
| 4. Action | None. Adequate treatment | Inefficient treatment. Follow up required. The treatment should be considered. |

Example 2

Correlation of Bioavailability and Immunogenicity of Adalimumab with the Clinical Response of Patients Suffering from Rheumatoid Arthritis Subjects: Rheumatoid arthritis patients, 49, fulfilling the 1987 ACR criteria and about to start treatment with adalimumab, were enrolled consecutively. 171 serum samples were analysed.

Treatment: Patients received doses of 40 mg of adalimumab (Humira®), subcutaneously, every two weeks.

Evaluation of the patient clinical response: DAS28 was used to evaluate the clinical response of the patient according scores in Table 1 (Example 1).

Bioavailability and immunogenicity correlation: Bioavailability and immunogenicity of adalimumab strongly correlate (p<0.05). Statistical correlation analysis was performed using Kendall's Tau-b and Sperman tests. Correlation results are shown in Table 13.

TABLE 13

Correlation between bioavailability and immunogenicity of adalimumab.

| | Kendall's Tau-b test | | Sperman test | |
|---|---|---|---|---|
| Parameter | Correlation coefficient | p-value | Correlation coefficient | p-value |
| Bioavailability Immunogenicity | −0.363 | 1.00E−06 | −0.444 | 1.00E−06 |

Clinical correlations: The correlation between bioavailability, immunogenicity and the disease activity based on the DAS28 values was analyzed. Clinical response strongly correlates with the level of free adalimumab (drug bioavailability) and antibodies against adalimumab (immunogenicity) (Table 14).

TABLE 14

Correlation between the adalimumab bioavailability, anti-adalimumab antibodies (immunogenicity) and DAS28.

| | Concentration of adalimumab (µg/ml) (Bioavailability) | Concentration of anti-adalimumab antibodies (AU/ml) (Immunogenicity) | DAS28 |
|---|---|---|---|
| Concentration of adalimumab (µg/ml) | — | −0.001 (171) | −0.001 (102) |
| Concentration of anti-adalimumab antibodies (AU/ml) | −0.001 (171) | — | 0.09 (102) |
| DAS28 | −0.001 (102) | 0.09 (102) | — |

A positive p value indicates a direct correlation.
A negative p value indicates an inverse correlation.
p values <0.05 or <−0.05 are statistically significant.
*p value of 0.06 is considered statistically significant. The value is very close to the significance criteria of p < 0.05, and therefore clinically relevant.

Determination of diagnostic cut-offs: According to the standard protocol to determine immunogenicity, there is never a positive titer of anti-adalimumab antibodies above 0.8 µg/ml of free adalimumab. Therefore, diagnostic cut-off was determined by measuring the anti-adalimumab antibodies concentration with the acid dissociation protocol in those samples with concentrations of free adalimumab below 0.8 µg/ml. 54 samples fulfilling this criteria were analysed. 22% of the patients with free adalimumab below 0.8 µg/ml showed a positive immunogenicity titer, and 77% of the patients with free adalimumab below the limit of detection (2 ng/ml) showed a positive immunogenicity titer (Table 15).

TABLE 15

Detection of antibodies anti-adalimumab using the acid dissociation protocol in samples with free adalimumab below 0.8 ug/ml and no antibodies against adalimumab.

| | Free adalimumab <2 ng/ml, no antibodies | | Free adalimumab <0.8 µg/ml, no antibodies | |
|---|---|---|---|---|
| | Samples # 28 | Patients # 18 | Samples # 26 | Patients # 13 |
| Positive after acid dissociation | 5 (18%) | 4 (22%) | 10 (38%) | 10 (77%) |

It was studied if there is a relationship between the level of free adalimumab below 0.8 µg/ml and the presence of antibodies anti-adalimumab above 8 AU/ml (equivalent to 32 ng/ml of antibodies) (limit of detection) with DAS28 (Table 16) in the whole cohort of patients.

TABLE 16

Disease activity as a function of bioavailability and immunogenicity cut-offs.

| Grouping | Average DAS28 | p-value |
|---|---|---|
| Adalimumab >0.8 µg/ml AND antibodies anti-adalimumab <8 AU/ml | 2.56 (53) | 0.037 |
| Adalimumab <0.8 µg/ml AND antibodies anti-adalimumab >8 AU/ml | 3.27 (4) | | p value <0.05 is statistically significant.

It is demonstrated that patients with an adalimumab bioavailability lower than 0.8 µg/ml and antibodies anti-adalimumab higher than 8 AU/ml (equivalent to 32 ng/ml of antibodies) show a higher DAS28 value compared to those with an adalimumab bioavailability higher than 0.8 µg/ml and antibodies anti-adalimumab lower than 8 AU/ml. This DAS28 difference is statistically significant.

Therefore, if a patient shows a combination of free adalimumab lower than (<) 0.8 µg/ml AND antibodies anti-adalimumab higher than (>) 8 AU/ml, there is a higher probability that the individual is a non-responder to the adalimumab treatment, showing a high activity of the disease (see EULAR guidelines on Table 1 and Table 16).

Accordingly, a patient showing a combination of free adalimumab equal to or higher than (≥) 0.8 µg/ml AND antibodies anti-adalimumab equal to or lower than (≤) 8 AU/ml has a higher probability of being a responder patient to the adalimumab treatment.

Adalimumab decision algorithm: It is demonstrated that the clinical response to adalimumab closely follows the drug levels and the presence of antibodies directed against the drug.

It is demonstrated that if a patient has a bioavailability value below 0.8 µg/ml AND an immunogenicity value above 8 AU/ml (equivalent to 32 ng/ml of antibodies), this will correlate with a higher probability of showing no clinical response to the treatment, therefore an increased DAS28 value (moderate or high disease activity) compared to those with bioavailability values above 0.8 µg/ml (p<0.001).

None of the analysed patients showed anti-adalimumab antibodies if the concentration of free adalimumab was above 0.8 µg/ml.

The following decision algorithm can be constructed from the data:

| 1. Analysis | Free adalimumab bioavailability determination AND anti-adalimumab antibodies analysis | |
| --- | --- | --- |
| 2. Result | Free adalimumab concentration ≥0.8 µg/ml AND anti-adalimumab antibodies ≤8 AU/ml | Free adalimumab concentration <0.8 µg/ml AND anti-adalimumab antibodies >8 AU/ml |
| 3. Patient classification | Responder | Non-responder |
| 4. Action | None. Adequate treatment | Inefficient treatment. Follow up required. The treatment should be considered. |

Example 3

Correlation of Bioavailability of Infliximab with the Clinical Response of Patients Suffering from Rheumatoid Arthritis Experiments were performed as described in Example 1 except that the anti-infliximab antibody levels were not analyzed. Thus, patients were classified according to the infliximab therapeutical cut-off.

Infliximab trough levels are significantly higher (2.73 µg/ml) in patients suffering from rheumatoid arthritis that show a good or moderate clinical response (responders) to the treatment (p=1E-09) compared to non-responders (0.002 µg/ml) after one year of treatment (Table 17).

TABLE 17

Comparison between trough infliximab levels according to response criteria.

| Patient classification | Median trough infliximab (µg/ml) | N | p |
| --- | --- | --- | --- |
| Responder | 2.73 | 71 | 1E–09 |
| Non-responder | 0.002 | 54 | |

To calculate the frequency of responders and non-responders rheumatoid arthritis patients after one year of treatment, we performed significance tests by Chi-squared analysis (Table 18). The number of patients that are classified as responders is significantly higher than non-responders when trough infliximab concentration is ≥1.5 µg/ml (p=3.55E-07). On the other hand, the number of patients that are classified as responders is significantly lower than non-responders when trough infliximab concentration is <1.5 µg/ml (p=0.028).

TABLE 18

Comparison of the frequency of responder and non-responder rheumatoid arthritis patients depending on the infliximab cut-off.

| Infliximab concentration | Patient classification | N | $p(\chi^2)$ |
| --- | --- | --- | --- |
| ≥1.5 µg/ml | Responder | 43 | 3.5E–07 |
| | Non-responder | 7 | |
| <1.5 µg/ml | Responder | 28 | 0.028 |
| | Non-responder | 47 | |

When trough infliximab concentration is ≥1.5 µg/ml, the median drug level of responder patients is 3.64 µg/ml, while is 2.68 µg/ml in the non-responder population (p=0.142). However, when trough infliximab concentration is <1.5 µg/ml, the median rug level of responder patients is significantly higher (0.06 µg/ml) than in the non-responder population (0.002 µg/ml) (p=4.23E-03) (Table 19).

TABLE 19

Median infliximab concentration for responder and non-responder populations depending on the infliximab cut-off.

| Infliximab concentration | Patient classification | N | Median | p(Kruskal-Wallis) |
| --- | --- | --- | --- | --- |
| ≥1.5 µg/ml | Responder | 43 | 3.6472 | 0.142 |
| | Non-responder | 7 | 2.688 | |
| <1.5 µg/ml | Responder | 28 | 0.0607 | 4.2E–03 |
| | Non-responder | 47 | 0.002 | |

Therefore, if a patient has an infliximab trough level <1.5 µg/ml it is more likely to have lost drug efficacy and be classified as a non-responder, therefore necessitating of a treatment regime revision. On the other hand, if a patient has an infliximab trough level ≥1.5 µg/ml it is more likely that the patient corresponds to a responder, since the patient is exposed to effective drug levels.

Example 4

Correlation of Bioavailability of Adalimumab with the Clinical Response of Patients Suffering from Rheumatoid Arthritis Experiments were performed as described in Example 2 except that the anti-adalimumab antibody levels were not analyzed. Thus, patients were classified according to the adalimumab therapeutical cut-off.

Adalimumab trough levels are significantly higher (12.25 µg/ml) in patients suffering from rheumatoid arthritis that show a good or moderate clinical response (responders) to the treatment (p=0.0005) compared to non-responders (4.15 µg/ml) after two years of treatment (Table 20).

TABLE 20

Comparison between trough adalimumab levels according to response criteria.

| Patient classification | Median trough adalimumab (µg/ml) | N | p |
|---|---|---|---|
| Responder | 12.25 | 16 | 0.0005 |
| Non-responder | 4.15 | 45 | |

To calculate the frequency of responder and non-responder rheumatoid arthritis patients after two years of treatment, we performed significance tests by Chi-squared analysis (Table 21). All patients with an adalimumab trough level <0.8 µg/ml are non-responders. No patients were classified as responders with adalimumab trough levels <0.8 µg/ml.

TABLE 21

Comparison of the frequency of responder and non-responder rheumatoid arthritis patients depending on the adalimumab cut-off.

| Adalimumab concentration | Patient | N | $p(\chi^2)$ |
|---|---|---|---|
| ≥0.8 µg/ml | Responder | 16 | 0.093 |
| | Non-responder | 27 | |
| <0.8 µg/ml | Responder | 0 | p < 0.05 |
| | Non-responder | 16 | |

When trough adalimumab concentration is ≥0.8 µg/ml, the median drug level of responder rheumatoid arthritis patients is 12.25 µg/ml, while is 6.73 µg/ml in the non-responder population (Table 22).

TABLE 22

Median adalimumab concentration of responder and non-responder populations depending on the adalimumab cut-off.

| Adalimumab concentration | Patient classification | N | Median | p(Kruskal-Wallis) |
|---|---|---|---|---|
| ≥0.8 µg/ml | Responder | 16 | 12.25 | 0.06 |
| | Non-responder | 27 | 6.73 | |
| <0.8 µg/ml | Responder | 0 | 0 | p < 0.05 |
| | Non-responder | 16 | 0.00008 | |

In conclusion, if a patient has an adalimumab trough level <0.8 µg/ml it is more likely to have lost drug efficacy and be classified as a non-responder, therefore necessitating of a treatment regime revision. On the other hand, if a patient has an adalimumab trough level ≥0.8 µg/ml there is an increased probability that the patient could be responding to the therapy.

The invention claimed is:

1. A method of treating a patient, comprising:
providing a patient sample, wherein (a) the patient sample is blood, plasma, or serum obtained from a patient suffering from rheumatoid arthritis and receiving a treatment comprising the administration to the patient of a biological drug selected from infliximab and adalimumab; (b) the patient has received at least one dose of the biological drug; and (c) the sample was obtained at a time t1 between two successive administrations of the biological drug;
determining the concentration of the biological drug in the patient sample; and
determining the concentration of antibodies against the biological drug in the patient sample;
comparing the concentration of the biological drug in the patient sample with a Reference Value 1 (RV1), wherein RV1 is a therapeutic efficiency cut-off value of the concentration of the circulating biological drug;
determining that the concentration of the biological drug in the patient sample is greater than or equal to RV1;
comparing the concentration of antibodies against the biological drug in the patient sample with a Reference Value 2 (RV2), wherein RV2 is a cut-off value of the concentration of the antibodies against the biological drug as determined in a group of treatment-naïve individuals;
determining that the concentration of antibodies against the biological drug in the patient sample is less than or equal to RV2;

classifying the patient as a responder to the biological drug; and re-administering the biological drug to the patient because the patient is classified as a responder, wherein:

the re-administering of the biological drug is the second of the two successive administrations of the biological drug;

when the biological drug is infliximab, then RV1 is 1.5 µg/ml and RV2 is 150 ng/ml; and when the biological drug is adalimumab, then RV1 is 0.8 µg/ml and RV2 is 32 ng/ml.

2. The method according to claim 1, wherein said t1 is a time point within two weeks of the administration of the biological drug.

3. The method according to claim 1, wherein the concentration of the circulating biological drug or the antibodies against the biological drug is determined by an immunoassay.

4. The method according to claim 3, wherein the immunoassay is an ELISA.

5. The method according to claim 1, wherein said t1 is a time point within one week of the administration of the biological drug.

6. A method for treating a patient suffering from rheumatoid arthritis, comprising:

administering to the patient a biological drug at a time, t1, wherein the biological drug is selected from infliximab and adalimumab;

determining the concentration of the circulating biological drug in a sample from the patient at a time, t1, wherein t1 is a time point after t1;

determining that the concentration of the circulating biological drug in the sample is greater than or equal to a Reference Value 1 (RV1);

determining the concentration of antibodies against the biological drug in the sample from the patient at t1;

determining that the concentration of the antibodies against the biological drug in the sample is less than or equal to a Reference Value 2 (RV2);

classifying the patient as a responder to the biological drug because the concentration of the biological drug in the sample is greater than or equal to RV1 and because the concentration of antibodies against the biological drug in the sample is less than or equal to RV2; and re-administering to the effective amount of the biological drug, because the patient is classified as a responder to the biological drug, wherein:

the sample is selected from a sample of blood, a sample of plasma, and a sample of serum;

RV1 is a therapeutic efficiency cut-off value of the concentration of the circulating biological drug;

RV2 is a cut-off value of the concentration of the antibodies against the biological drug as determined in a group of treatment-naive individuals;

when the biological drug is infliximab, then RV1 is 1.5 µg/ml and RV2 is 150 nq/ml; and when the biological drug is adalimumab, then RV1 is 0.8 µg/ml and RV2 is 32 ng/ml.

7. The method according to claim 6, wherein t1 is a time point within two weeks of ti.

8. The method according to 6, wherein t1 is a time point within one week of ti.

9. The method according to claim 6, wherein the concentration of the circulating biological drug or antibodies against the biological drug is determined by an immunoassay.

10. The method according to claim 9, wherein the immunoassay is an ELISA.

11. A method of treating a human patient suffering from rheumatoid arthritis, wherein the patient is receiving a biological drug selected from infliximab and adalimumab, comprising:

detecting the concentration of the biological drug in a blood, plasma, or serum sample obtained from the subject, determining that the detected concentration of the biological drug in the sample is greater than or equal to a Reference Value 1 (RV1);

detecting the concentration of antibodies against the biological drug in the sample; and determining that if the detected concentration of antibodies against the biological drug in the sample is less than or equal to a Reference Value 2 (RV2);

and classifying the patient as a responder to the biological drug; and re-administering the biological drug to the patient, wherein:

the patient would not have been classified as a responder and the biological drug would not have been re-administered to the patient if both the detected concentration of the biological drug in the patient sample were less than RV1 and the concentration of antibodies against the biological drug in the patient sample were greater than RV2; and when the biological drug is infliximab, then RV1 is 1.5 µg/ml and RV2 is 150 ng/ml; or when the biological drug is adalimumab, then RV1 is 0.8 µg/ml and RV2 is 32 ng/ml.

* * * * *